United States Patent
Bruneau et al.

(10) Patent No.: US 8,034,079 B2
(45) Date of Patent: Oct. 11, 2011

(54) IMPLANTS AND METHODS FOR POSTERIOR DYNAMIC STABILIZATION OF A SPINAL MOTION SEGMENT

(75) Inventors: Aurelien Bruneau, Memphis, TN (US); Tommy Carls, Memphis, TN (US); Eric C. Lange, Collierville, TN (US); Fred J. Molz, IV, Collierville, TN (US); Matthew M. Morrison, Cordova, TN (US); Jonathan Dewey, Memphis, TN (US); Kent M. Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 154 days.

(21) Appl. No.: 11/104,350

(22) Filed: Apr. 12, 2005

(65) Prior Publication Data

US 2006/0241614 A1 Oct. 26, 2006

(51) Int. Cl.
*A61B 17/70* (2006.01)
(52) U.S. Cl. ........................................... 606/249
(58) Field of Classification Search .............. 623/16.11, 623/17.11–17.16; 606/61, 246–249
See application file for complete search history.

(56) References Cited

U.S. PATENT DOCUMENTS

| | | | |
|---|---|---|---|
| 278,097 A | 5/1883 | Collins |
| 624,969 A | 5/1899 | Peterson |
| 1,153,797 A | 9/1915 | Kegreisz |
| 1,516,347 A | 11/1924 | Pataky |
| 1,706,431 A | 3/1929 | Whitliff |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,502,902 A | 4/1950 | Tofflemire |
| 2,607,370 A | 8/1952 | Anderson |
| 2,677,369 A | 5/1954 | Knowles |
| 2,685,877 A | 8/1954 | Dobelle |
| 2,774,350 A | 12/1956 | Cleveland, Jr. |
| 3,065,659 A | 11/1962 | Eriksson et al. |
| 3,108,595 A | 10/1963 | Overment |
| 3,123,077 A | 3/1964 | Alcamo |
| 3,397,699 A | 8/1968 | Kohl |
| 3,426,364 A | 2/1969 | Lumb |
| 3,648,691 A | 3/1972 | Lumb et al. |
| 3,654,668 A | 4/1972 | Appleton |
| 3,678,542 A | 7/1972 | Prete, Jr. |
| 3,693,616 A | 9/1972 | Roaf et al. |
| 3,779,239 A | 12/1973 | Fischer et al. |

(Continued)

FOREIGN PATENT DOCUMENTS

DE 2821678 A1 11/1979

(Continued)

OTHER PUBLICATIONS

Posterior Spinal Instrumentation for Thoracolumbar Tumor and Trauma Reconstruction, Seminars in Spine Surgery, vol. 9, No. 3, Sep. 1997, pp. 260-277.

(Continued)

*Primary Examiner* — Eduardo C Robert
*Assistant Examiner* — Tara Carter (57) ABSTRACT

An implant assembly for stabilizing a spinal motion segment includes a spacer member positionable between adjacent spinous processes and upper and lower engaging members extending from the spacer member. The upper and lower engaging members engage at least one lamina to resist flexion of the spinal motion segment.

4 Claims, 3 Drawing Sheets

U.S. PATENT DOCUMENTS

| | | | |
|---|---|---|---|
| 4,003,376 A | 1/1977 | McKay et al. | |
| 4,011,602 A | 3/1977 | Rybicki et al. | |
| 4,047,523 A | 9/1977 | Hall | |
| 4,237,875 A | 12/1980 | Termanini | |
| 4,257,409 A | 3/1981 | Bacal et al. | |
| 4,274,324 A | 6/1981 | Giannuzzi | |
| 4,289,123 A | 9/1981 | Dunn | |
| 4,327,736 A | 5/1982 | Inoue | |
| 4,401,112 A | 8/1983 | Rezaian | |
| 4,422,451 A | 12/1983 | Kalamchi | |
| 4,448,191 A | 5/1984 | Rodnyansky et al. | |
| 4,499,636 A | 2/1985 | Tanaka | |
| 4,519,100 A | 5/1985 | Wills et al. | |
| 4,553,273 A | 11/1985 | Wu | |
| 4,554,914 A | 11/1985 | Kapp et al. | |
| 4,570,618 A | 2/1986 | Wu | |
| 4,573,454 A | 3/1986 | Hoffman | |
| 4,592,341 A | 6/1986 | Omagari et al. | |
| 4,599,086 A | 7/1986 | Doty | |
| 4,604,995 A | 8/1986 | Stephens et al. | |
| 4,611,582 A | 9/1986 | Duff | |
| 4,632,101 A | 12/1986 | Freedland | |
| 4,636,217 A | 1/1987 | Ogilvie et al. | |
| 4,643,174 A | 2/1987 | Horiuchi | |
| 4,643,178 A | 2/1987 | Nastari et al. | |
| 4,646,998 A | 3/1987 | Pate | |
| 4,657,550 A | 4/1987 | Daher | |
| 4,662,808 A | 5/1987 | Camilleri | |
| 4,686,970 A | 8/1987 | Dove et al. | |
| 4,704,057 A | 11/1987 | McSherry | |
| 4,721,103 A | 1/1988 | Freedland | |
| 4,759,769 A | 7/1988 | Hedman et al. | |
| 4,776,851 A | 10/1988 | Bruchman et al. | |
| 4,779,816 A | 10/1988 | Varlet | |
| 4,787,378 A | 11/1988 | Sodhi | |
| 4,822,226 A | 4/1989 | Kennedy | |
| 4,827,918 A | 5/1989 | Olerud | |
| 4,834,600 A | 5/1989 | Lemke | |
| 4,841,959 A | 6/1989 | Ransford | |
| 4,863,476 A | 9/1989 | Shepperd | |
| 4,886,405 A | 12/1989 | Blomberg | |
| 4,892,545 A | 1/1990 | Day et al. | |
| 4,913,134 A | 4/1990 | Luque | |
| 4,913,144 A | 4/1990 | Del Medico | |
| 4,931,055 A | 6/1990 | Bumpus et al. | |
| 4,932,975 A | 6/1990 | Main et al. | |
| 4,969,887 A | 11/1990 | Sodhi | |
| 4,998,936 A | 3/1991 | Mehdian | |
| 5,000,166 A | 3/1991 | Karpf | |
| 5,010,879 A | 4/1991 | Moriya et al. | |
| 5,011,484 A * | 4/1991 | Breard | 606/249 |
| 5,030,220 A | 7/1991 | Howland | |
| 5,047,055 A | 9/1991 | Bao et al. | |
| 5,059,193 A | 10/1991 | Kuslich | |
| 5,092,866 A | 3/1992 | Breard et al. | |
| 5,098,433 A | 3/1992 | Freedland | |
| 5,171,278 A | 12/1992 | Pisharodi | |
| 5,180,393 A | 1/1993 | Commarmond | |
| 5,201,734 A | 4/1993 | Cozad et al. | |
| 5,267,999 A | 12/1993 | Olerud | |
| 5,290,312 A | 3/1994 | Kojimoto et al. | |
| 5,306,275 A | 4/1994 | Bryan | |
| 5,306,310 A | 4/1994 | Siebels | |
| 5,312,405 A | 5/1994 | Korotko et al. | |
| 5,316,422 A | 5/1994 | Coffman | |
| 5,356,412 A | 10/1994 | Golds et al. | |
| 5,356,417 A | 10/1994 | Golds | |
| 5,356,423 A | 10/1994 | Tihon et al. | |
| 5,360,430 A | 11/1994 | Lin | |
| 5,366,455 A * | 11/1994 | Dove et al. | 606/61 |
| 5,370,697 A | 12/1994 | Baumgartner | |
| 5,390,683 A | 2/1995 | Pisharodi | |
| 5,395,370 A | 3/1995 | Muller et al. | |
| 5,401,269 A | 3/1995 | Buttner-Janz et al. | |
| 5,403,316 A | 4/1995 | Ashman | |
| 5,415,661 A | 5/1995 | Holmes | |
| 5,437,672 A | 8/1995 | Alleyne | |
| 5,437,674 A | 8/1995 | Worcel et al. | |
| 5,439,463 A | 8/1995 | Lin | |
| 5,454,812 A | 10/1995 | Lin | |
| 5,456,689 A | 10/1995 | Kresch et al. | |
| 5,458,641 A | 10/1995 | Ramirez Jimenez | |
| 5,480,442 A | 1/1996 | Bertagnoli | |
| 5,496,318 A | 3/1996 | Howland et al. | |
| 5,518,498 A | 5/1996 | Lindenberg et al. | |
| 5,527,312 A * | 6/1996 | Ray | 606/61 |
| 5,554,191 A | 9/1996 | Lahille et al. | |
| 5,562,662 A | 10/1996 | Brumfield et al. | |
| 5,562,735 A | 10/1996 | Margulies | |
| 5,571,192 A | 11/1996 | Schonhoffer | |
| 5,575,819 A | 11/1996 | Amis | |
| 5,609,592 A | 3/1997 | Brumfield et al. | |
| 5,609,634 A | 3/1997 | Voydeville | |
| 5,609,635 A | 3/1997 | Michelson | |
| 5,628,756 A | 5/1997 | Barker, Jr. et al. | |
| 5,630,816 A | 5/1997 | Kambin | |
| 5,645,599 A | 7/1997 | Samani | |
| 5,653,762 A | 8/1997 | Pisharodi | |
| 5,653,763 A | 8/1997 | Errico et al. | |
| 5,658,335 A | 8/1997 | Allen | |
| 5,665,096 A | 9/1997 | Yoon | |
| 5,665,122 A | 9/1997 | Kambin | |
| 5,674,295 A | 10/1997 | Ray et al. | |
| 5,676,702 A | 10/1997 | Ratron | |
| 5,685,826 A | 11/1997 | Bonutti | |
| 5,690,649 A | 11/1997 | Li | |
| 5,693,100 A | 12/1997 | Pisharodi | |
| 5,702,395 A | 12/1997 | Hopf | |
| 5,702,452 A | 12/1997 | Argenson et al. | |
| 5,702,455 A | 12/1997 | Saggar | |
| 5,707,390 A | 1/1998 | Bonutti | |
| 5,716,416 A | 2/1998 | Lin | |
| 5,723,013 A | 3/1998 | Jeanson et al. | |
| 5,725,341 A | 3/1998 | Hofmeister | |
| 5,725,582 A | 3/1998 | Bevan et al. | |
| 5,746,762 A | 5/1998 | Bass | |
| 5,755,797 A | 5/1998 | Baumgartner | |
| 5,797,916 A | 8/1998 | McDowell | |
| 5,800,547 A | 9/1998 | Schafer et al. | |
| 5,810,815 A | 9/1998 | Morales | |
| 5,836,948 A | 11/1998 | Zucherman et al. | |
| 5,849,004 A | 12/1998 | Bramlet | |
| 5,860,977 A | 1/1999 | Zucherman et al. | |
| 5,885,290 A | 3/1999 | Guerrero et al. | |
| 5,888,196 A | 3/1999 | Bonutti | |
| 5,941,881 A | 8/1999 | Barnes | |
| 5,976,186 A | 11/1999 | Bao et al. | |
| 5,980,523 A | 11/1999 | Jackson | |
| 6,022,376 A | 2/2000 | Assell et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,090,043 A | 7/2000 | Austin et al. | |
| 6,126,689 A | 10/2000 | Brett | |
| 6,126,691 A | 10/2000 | Kasra et al. | |
| 6,127,597 A | 10/2000 | Beyar et al. | |
| 6,132,464 A | 10/2000 | Martin | |
| 6,190,413 B1 | 2/2001 | Sutcliffe | |
| 6,190,414 B1 | 2/2001 | Young | |
| 6,214,037 B1 | 4/2001 | Mitchell et al. | |
| 6,214,050 B1 | 4/2001 | Huene | |
| 6,245,107 B1 | 6/2001 | Ferree | |
| 6,293,949 B1 | 9/2001 | Justis et al. | |
| 6,312,431 B1 | 11/2001 | Asfora | |
| 6,336,930 B1 | 1/2002 | Stalcup et al. | |
| 6,348,053 B1 | 2/2002 | Cachia | |
| 6,352,537 B1 | 3/2002 | Strnad | |
| 6,364,883 B1 | 4/2002 | Santilli | |
| 6,371,987 B1 | 4/2002 | Weiland et al. | |
| 6,375,682 B1 | 4/2002 | Fleischmann et al. | |
| 6,402,750 B1 | 6/2002 | Atkinson et al. | |
| 6,402,751 B1 | 6/2002 | Hoeck et al. | |
| 6,419,703 B1 | 7/2002 | Fallin et al. | |
| 6,419,704 B1 | 7/2002 | Ferree | |
| 6,432,130 B1 | 8/2002 | Hanson | |
| 6,440,169 B1 | 8/2002 | Elberg et al. | |
| 6,447,513 B1 | 9/2002 | Griggs | |

| | | |
|---|---|---|
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,255 B1* | 2/2003 | Ferree .................. 606/61 |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1* | 9/2003 | Taylor .................. 623/17.16 |
| 6,645,207 B2 | 11/2003 | Dixon et al. |
| 6,652,527 B2* | 11/2003 | Zucherman et al. ........ 606/61 |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,524,324 B2 | 4/2009 | Winslow et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,901,430 B2 | 3/2011 | Matsuura et al. |
| 2001/0016743 A1 | 8/2001 | Zucherman et al. |
| 2002/0029039 A1* | 3/2002 | Zucherman et al. ........ 606/61 |
| 2002/0143331 A1 | 10/2002 | Zucherman et al. |
| 2003/0032959 A1* | 2/2003 | Yeh .................. 606/61 |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2003/0216736 A1 | 11/2003 | Robinson et al. |
| 2004/0010312 A1 | 1/2004 | Enayati |
| 2004/0010316 A1 | 1/2004 | William et al. |
| 2004/0087947 A1 | 5/2004 | Lim et al. |
| 2004/0097931 A1 | 5/2004 | Mitchell |
| 2004/0106995 A1 | 6/2004 | Le Couedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0167625 A1 | 8/2004 | Beyar et al. |
| 2004/0181282 A1 | 9/2004 | Zucherman et al. |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1* | 2/2005 | Berry .................. 623/17.14 |
| 2005/0049708 A1 | 3/2005 | Atkinson et al. |
| 2005/0055031 A1 | 3/2005 | Lim |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0209603 A1 | 9/2005 | Zucherman et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Feree |
| 2006/0004447 A1 | 1/2006 | Mastrorio et al. |
| 2006/0004455 A1 | 1/2006 | Leonard et al. |
| 2006/0015099 A1* | 1/2006 | Cannon et al. .................. 606/61 |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1* | 5/2006 | Ferree et al. .................. 606/61 |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0149242 A1 | 7/2006 | Kraus et al. |
| 2006/0149278 A1 | 7/2006 | Abdou |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235386 A1 | 10/2006 | Anderson |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241610 A1 | 10/2006 | Lim et al. |
| 2006/0241613 A1 | 10/2006 | Bruneau et al. |
| 2006/0241614 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |

| | | | |
|---|---|---|---|
| 2007/0142915 A1 | 6/2007 | Altarac et al. | |
| 2007/0151116 A1 | 7/2007 | Malandain | |
| 2007/0162000 A1 | 7/2007 | Perkins | |
| 2007/0167945 A1 | 7/2007 | Lange et al. | |
| 2007/0173822 A1 | 7/2007 | Bruneau et al. | |
| 2007/0173823 A1 | 7/2007 | Dewey et al. | |
| 2007/0191833 A1 | 8/2007 | Bruneau et al. | |
| 2007/0191834 A1 | 8/2007 | Bruneau et al. | |
| 2007/0191837 A1 | 8/2007 | Trieu | |
| 2007/0191838 A1 | 8/2007 | Bruneau et al. | |
| 2007/0198091 A1 | 8/2007 | Boyer et al. | |
| 2007/0225807 A1 | 9/2007 | Phan et al. | |
| 2007/0233068 A1 | 10/2007 | Bruneau et al. | |
| 2007/0233074 A1 | 10/2007 | Anderson et al. | |
| 2007/0233076 A1 | 10/2007 | Trieu | |
| 2007/0233081 A1 | 10/2007 | Pasquet et al. | |
| 2007/0233089 A1 | 10/2007 | DiPoto et al. | |
| 2007/0250060 A1 | 10/2007 | Anderson et al. | |
| 2007/0270823 A1 | 11/2007 | Trieu et al. | |
| 2007/0270824 A1 | 11/2007 | Lim et al. | |
| 2007/0270825 A1 | 11/2007 | Carls et al. | |
| 2007/0270826 A1 | 11/2007 | Trieu et al. | |
| 2007/0270827 A1 | 11/2007 | Lim et al. | |
| 2007/0270828 A1 | 11/2007 | Bruneau et al. | |
| 2007/0270829 A1 | 11/2007 | Carls et al. | |
| 2007/0270834 A1 | 11/2007 | Bruneau et al. | |
| 2007/0270874 A1 | 11/2007 | Anderson | |
| 2007/0272259 A1 | 11/2007 | Allard et al. | |
| 2007/0276368 A1 | 11/2007 | Trieu et al. | |
| 2007/0276369 A1 | 11/2007 | Allard et al. | |
| 2007/0276493 A1 | 11/2007 | Malandain et al. | |
| 2007/0276496 A1 | 11/2007 | Lange et al. | |
| 2007/0276497 A1 | 11/2007 | Anderson | |
| 2007/0282443 A1 | 12/2007 | Globerman et al. | |
| 2008/0009866 A1 | 1/2008 | Alamin et al. | |
| 2008/0015693 A1 | 1/2008 | Le Couedic | |
| 2008/0021457 A1 | 1/2008 | Anderson et al. | |
| 2008/0021460 A1 | 1/2008 | Bruneau et al. | |
| 2008/0058934 A1 | 3/2008 | Malandain et al. | |
| 2008/0097446 A1 | 4/2008 | Reiley et al. | |
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0183209 A1 | 7/2008 | Robinson et al. | |
| 2008/0183211 A1 | 7/2008 | Lamborne et al. | |
| 2008/0183218 A1 | 7/2008 | Mueller et al. | |
| 2008/0195152 A1 | 8/2008 | Altarac et al. | |
| 2008/0215094 A1 | 9/2008 | Taylor | |
| 2008/0221685 A9 | 9/2008 | Altarac et al. | |
| 2008/0234824 A1 | 9/2008 | Youssef et al. | |
| 2008/0262617 A1 | 10/2008 | Froehlich et al. | |
| 2008/0281360 A1 | 11/2008 | Vittur et al. | |
| 2008/0281361 A1 | 11/2008 | Vittur et al. | |
| 2009/0018658 A1 | 1/2009 | Garcia | |
| 2009/0062915 A1 | 3/2009 | Kohm et al. | |
| 2009/0105766 A1 | 4/2009 | Thompson et al. | |
| 2009/0105773 A1 | 4/2009 | Lange et al. | |
| 2009/0234389 A1 | 9/2009 | Chuang et al. | |
| 2009/0240283 A1 | 9/2009 | Carls et al. | |
| 2009/0270918 A1 | 10/2009 | Attia et al. | |
| 2010/0121379 A1 | 5/2010 | Edmond | |
| 2010/0204732 A1 | 8/2010 | Aschmann et al. | |

FOREIGN PATENT DOCUMENTS

| | | | |
|---|---|---|---|
| DE | 3922044 A1 | 2/1991 | |
| DE | 4012622 C1 | 7/1991 | |
| EP | 0322334 B1 | 2/1992 | |
| EP | 0767636 B1 | 1/1999 | |
| EP | 1004276 A1 | 5/2000 | |
| EP | 1011464 B1 | 6/2000 | |
| EP | 1138268 A1 | 10/2001 | |
| EP | 1148850 B1 | 10/2001 | |
| EP | 1148851 B1 | 10/2001 | |
| EP | 1302169 A1 | 4/2003 | |
| EP | 1330987 A1 | 7/2003 | |
| EP | 1552797 A2 | 7/2005 | |
| EP | 1854433 A1 | 11/2007 | |
| EP | 1905392 A1 | 4/2008 | |
| EP | 1982664 A1 | 10/2008 | |
| FR | 2623085 A1 | 5/1989 | |
| FR | 2625097 A1 | 6/1989 | |
| FR | 2681525 A1 | 3/1993 | |
| FR | 2700941 A1 | 8/1994 | |
| FR | 2703239 A1 | 10/1994 | |
| FR | 2707864 A1 | 1/1995 | |
| FR | 2717675 A1 | 9/1995 | |
| FR | 2722087 A1 | 1/1996 | |
| FR | 2722088 A1 | 1/1996 | |
| FR | 2724554 A1 | 3/1996 | |
| FR | 2725892 A1 | 4/1996 | |
| FR | 2730156 A1 | 8/1996 | |
| FR | 2731643 A1 | 9/1996 | |
| FR | 2 775 183 A1 | 2/1998 | |
| FR | 2775183 A1 | 8/1999 | |
| FR | 2 799 640 A1 | 10/1999 | |
| FR | 2799948 A1 | 4/2001 | |
| FR | 2816197 A1 | 5/2002 | |
| GB | 780652 | 8/1957 | |
| JP | 02-224660 | 9/1990 | |
| JP | 09-075381 | 3/1997 | |
| JP | 2003-079649 | 3/2003 | |
| SU | 988281 | 1/1983 | |
| SU | 1484348 A1 | 6/1989 | |
| WO | WO 94/26192 | 11/1994 | |
| WO | WO 94/26195 | 11/1994 | |
| WO | 97/18769 | 5/1997 | |
| WO | WO 98/20939 | 5/1998 | |
| WO | WO 99/26562 | 6/1999 | |
| WO | WO 00/44319 | 8/2000 | |
| WO | WO 01/54598 A1 | 8/2001 | |
| WO | WO 02/71960 A1 | 3/2002 | |
| WO | WO 03/057055 A1 | 7/2003 | |
| WO | WO 2004/047689 A1 | 6/2004 | |
| WO | WO 2004/047691 A1 | 6/2004 | |
| WO | 2004/084743 A1 | 10/2004 | |
| WO | 2004/084768 A2 | 10/2004 | |
| WO | WO 2004084743 A1 * | 10/2004 | |
| WO | 2004/110300 A2 | 12/2004 | |
| WO | WO 2005/009300 A1 | 2/2005 | |
| WO | WO 2005/011507 A1 | 2/2005 | |
| WO | 2005/037150 A1 | 4/2005 | |
| WO | WO 2005/044118 A1 | 5/2005 | |
| WO | WO 2005/048856 A1 | 6/2005 | |
| WO | WO 2005/110258 A1 | 11/2005 | |
| WO | 2006/064356 A1 | 6/2006 | |
| WO | WO 2007/034516 A1 | 3/2007 | |
| WO | 2007/052975 A1 | 5/2007 | |
| WO | 2009/083276 A1 | 7/2009 | |
| WO | 2009/083583 A1 | 7/2009 | |
| WO | 2009/098536 A1 | 8/2009 | |

OTHER PUBLICATIONS

Reduction and Fixation of Late Diagnosed Lower Cervical Spine Dislocations Using the Daab Plate, Archives of Orthopaedic and Traumatic Surgery, 1984, pp. 353-355.

Posterior Spinal Fusion Using Internal Fixation with the Daab Plate, Act. Orthop. Scand. 55, pp. 310-314, 1984.

The Value of the Wilson Plate in Spinal Fusion, M.C. Cobey, M.D., May 1971.

"Dispositivo Intervertebrale Ammortizzante DIAM," date unknown, p. 1.

"Tecnica Operatoria Per Il Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Societá di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfó, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative á la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopéedique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp, 244-249, Medical, 1990.

Zdeblick et al., "Two-Point Fixation of the Lumbar Spine Differential Stability in Rotation," SPINE, 1991, pp. 5298-5301, vol. 16, No. 6, Supplement.

Anasetti et al., "Spine Stability After Implantation of an interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Disord, Tech., 2006, vol. 00, No. 00, pp. 1-7.

Buric et al., "DIAM Device For Low Back Pain In Degenerative Disc Disease 24 Months Follow-up" Advances in Minimally Invasive Surgery And Therapy For Spine And Nerves, Alexandre et al., eds., 2011, pp. 177-182, Spinger-Veriat/Wien.

Phillips et al., "Biomechanics of Posterior Dynamic Stabilizing Device (DIAM) Facetectomy and Discectomy," The Spine Journal, 2006, vol. 6, pp, 714-722.

Taylor et al., "Device For Intervertebral Assisted Motion; Technique and Initial Results," Neurosurg. Focus, Jan. 2007, vol. 22, No. 1, pp. 1-6.

Wilke et al., "Biomechanical Effect of Different Lumbar Interspinous Implants on Flexibility and intradiscal Pressure," Eur. Spine J., vol. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

* cited by examiner

IMPLANTS AND METHODS FOR POSTERIOR DYNAMIC STABILIZATION OF A SPINAL MOTION SEGMENT

BACKGROUND

Implants can be positioned between adjacent spinous processes to provide resistance to vertebral movement as a result of extension of the spinal column. These implants can provide a shock absorber or bumper that dynamically limits spinal extension. The implants can be secured to the adjacent spinous processes with looped cables or straps that extend completely about the spinous processes and implant to maintain positioning of the implant between the spinous processes while also limiting spinal flexion. However, these looped cables or straps can cut into the bone along the superior or inferior surfaces of the respective spinous process when subjected to sufficient forces. Furthermore, the looped cables or straps can be exposed to the spinal foramen at the location between the spinous processes, providing a potential for entry or impingement into the spinal foramen.

SUMMARY

There is provided a spinal implant assembly including a spacer member positionable between adjacent spinous processes with ends contacting respective ones of the spinous processes to limit extension of a spinal motion segment and engaging members coupled to the spinal motion segment to limit flexion. At least one of the engaging members is structured to contact a surface of a lamina opposite the spinous process surface in contact with the end of the spacer member.

According to one aspect, a spinal implant assembly includes a spacer member extending between opposite first and second ends positionable between adjacent upper and lower spinous processes of a spinal motion segment. The spacer member includes a compressible body to dynamically limit movement of the upper and lower spinous processes toward one another upon extension of the spinal motion segment. An upper engaging member and a lower engaging member each extend from the spacer member and are engageable with the spinal motion segment to limit flexion of the spinal motion segment. At least one of the upper and lower engaging members are structured for positioning along a surface of a lamina adjacent a respective one of the upper and lower spinous processes. The lamina surface is opposite a surface of the respective spinous process in contact with the adjacent one of the first and second ends of the spacer member.

In another aspect, a spinal implant assembly includes a spacer member extending between opposite first and second ends positionable between adjacent upper and lower spinous processes of a spinal motion segment. The spacer member includes a compressible body to dynamically limit movement of the upper and lower spinous processes toward one another under extension of the spinal motion segment. An upper engaging member and a lower engaging member extend from respective ones of the first and second ends of the spacer member. The upper engaging member includes a hook end portion positionable along a superior surface of an upper lamina adjacent the upper spinous process and the lower engaging member including a hook end portion positionable along an inferior surface of the lower spinous process. The engaging members contact the respective lamina surfaces to limit flexion of the spinal motion segment.

In a further aspect, a method for stabilizing a spinal motion segment comprises: positioning a spacer member between adjacent upper and lower spinous processes of the spinal motion segment, the spacer member including an upper end contacting an inferior surface of the upper spinous process and a lower end contacting a superior surface of the lower spinous process; positioning an upper engaging member extending from the upper end of the spacer member in contact with a superior surface of an upper lamina adjacent the upper spinous process; and positioning a lower engaging member extending the lower end of the spacer member in contact with an inferiorly oriented surface adjacent the lower spinous process.

According to another aspect, as spinal implant assembly includes a spacer member extending between opposite first and second ends positionable between adjacent upper and lower spinous processes of a spinal motion segment. The first and second ends each include a pair of arms extending along opposite sides of the adjacent spinous process. The spacer member includes a compressible body to dynamically limit movement of the upper and lower spinous processes toward one another upon extension of the spinal motion segment. The assembly further includes a first engaging member and a second engaging member each extending from the spacer member and engageable with the spinal motion segment to limit flexion of the spinal motion segment. The first engaging member is engaged with the spacer member along one of the arms at the first end and the second engaging member is engaged with the spacer member along one of the arms at the second end.

These and other aspects will be discussed further below.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Implants are positionable between adjacent spinous processes of a spinal motion segment to dynamically stabilize and limit spinal extension and flexion. The implant includes a spacer member received between the spinous processes that is compressible to allow extension motion of the motion segment while maintaining a distraction force between the spinous processes. The implant further includes engaging members extending from each of the upper and lower ends of the spacer member. The engaging members engage the spinal motion segment to limit flexion. At least one of the engaging members is structured to engage a surface of the lamina adjacent the respective spinous process. The lamina provides a stable support surface suited to resisting loads applied thereto by the implant in resisting flexion of the motion segment. Engagement of the lamina with the engaging member also reduces torsional loading on the posterior vertebral elements.

In another embodiment, each of the upper and lower engaging members of the implant assembly is engageable along a surface of a lamina adjacent the respective spinous process. The engaging members engage surfaces of the lamina opposite the surfaces of the spinous process supported by the respective end of the spacer member. In a further embodiment, the engaging members include hooked ends, and the hooked end of the upper engaging member extends along the superior surface of the upper lamina and the hooked end of the lower engaging member extends along the inferior surface of the lower member. In another embodiment, the engaging members are movably coupled with the spacer member. In yet another embodiment, at least one of the upper and lower engaging members includes a resilient connecting portion allowing limited flexion of the motion segment while maintain engagement of the engaging member with the lamina.

Figure 1:
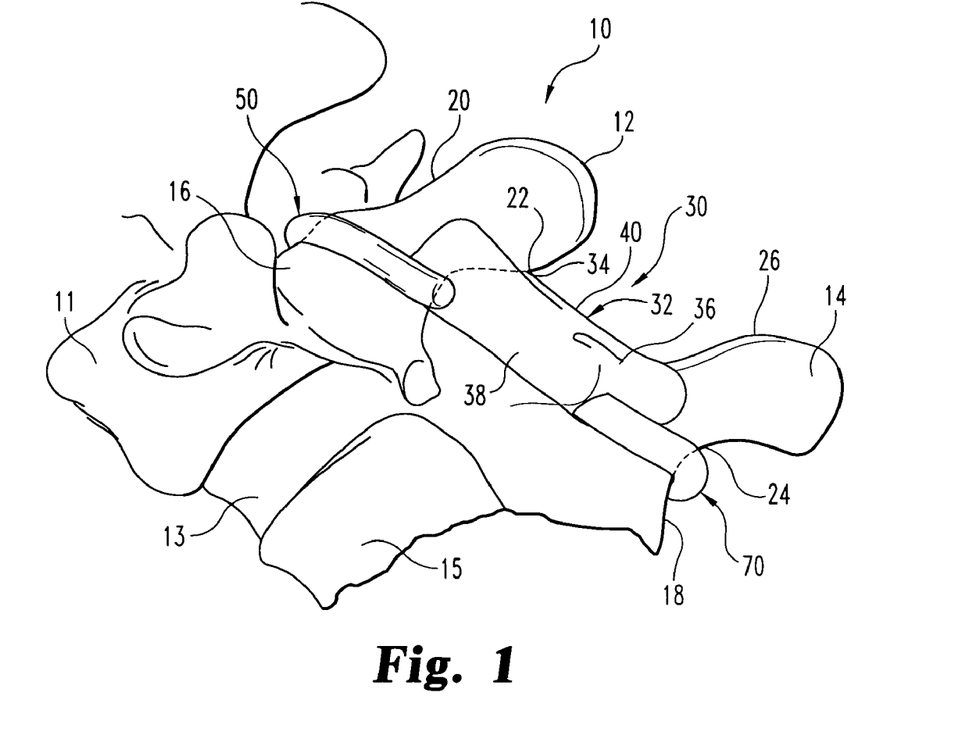
FIG. 1 is a perspective view of a posterior portion of spinal column motion segment with an implant assembly engaged thereto.

In FIG. 1 there is shown a spinal column segment 10 including an upper vertebra 11, a lower vertebra 15 and a spinal disc 13 therebetween. The vertebrae 11, 15 and disc 13 comprise a spinal motion segment, it being understood that a spinal motion segment may include multiple vertebral levels. Upper vertebra 11 includes an upper spinous process 12 extending from an upper lamina 16. Lower vertebra 15 includes a lower spinous process 14 extending from a lower lamina 18. The spinous processes 12, 14 and laminae 16, 18 comprise posterior elements of the vertebrae of the spinal motion segment.

A spinal implant assembly 30 is positioned in engagement with the posterior vertebral elements to provide dynamic spinal stabilization. Spinal implant assembly 30 includes a spacer member 32 extending between and contacting adjacent surfaces of spinous processes 12, 14 to limit movement of the spinous processes toward one another as a result of extension of the spinal motion segment. For example, spacer member 32 can include an upper end 34 in contact with inferior surface 22 of spinous process 12, and a lower end 36 in contact with superior surface 26 of spinous process 14. Spacer member 32 can include a body structured to resiliently compress in response to extension of the spinal motion segment, providing resistance to the extension forces and limiting movement of the spinous processes 12, 14 toward one another as spacer member 32 is compressed.

Figure 2:
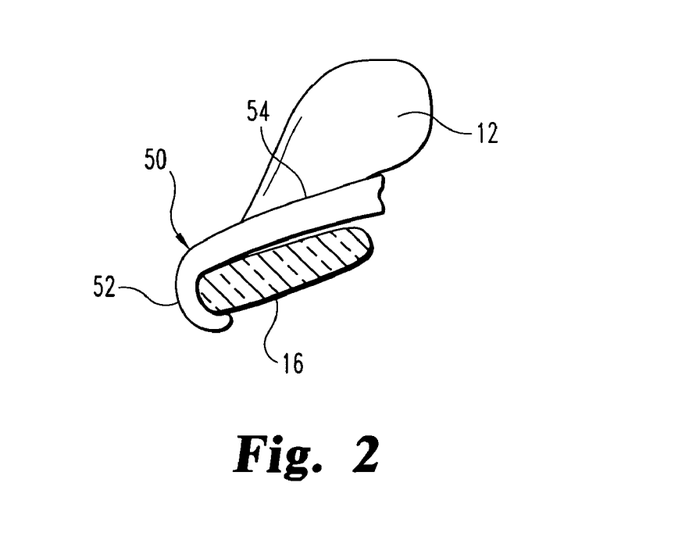
FIG. 2 is an enlarged view of a portion of the spinal motion segment of FIG. 1 showing an engaging member of the implant assembly and a lamina.

Implant assembly 30 includes an upper engaging member 50 and a lower engaging member 70 extending from spacer member 32. Upper engaging member 50 extends along and contacts a superior surface 20 of upper lamina 16, and lower engaging member 70 extends along and contacts an inferior surface 24 of lower lamina 18. Engaging member 50, 70 thus limit movement of the spinous processes 12, 14 away from one another as a result of flexion of the motion segment. In one embodiment, engaging members 50, 70 are movably coupled with spacer member 32 to facilitate manipulation of the engaging members 50, 70 and placement over the spinal lamina. For example, as shown in FIG. 2, engaging member 50 includes a connecting portion 54 extending from spacer member 32 and a hook end portion 52 positionable along a superior surface of lamina 16. Engagement of the hook end portion 52 with the spinal lamina provides a bony support surface of sufficient size and strength to allow the forces exerted by engaging members 50, 70 to be resisted without cracking, cutting, or otherwise unsuitably deforming the bone.

In order to facilitate positioning of engaging members 50, 70 along the respective lamina 16, 18, engaging members 50, 70 can be offset toward the anterior side 38 of spacer member 32. Posterior side 40 of spacer member 32 is oriented posteriorly between spinous processes 12, 14. Since ends 34, 36 engage the adjacent surface of the respective spinous processes 12, 14, positioning engaging members 50, 70 along the anterior side 38 facilitates engagement with the respective laminae 16, 18, which are each located anteriorly of the respective adjacent spinous process 12, 14.

In one embodiment, engaging member 50 includes a flexible connecting portion 54 and a rigid hook end portion 52. The flexible connecting portion 54 facilitates manipulation of the engaging member 50 relative to spacer member 32 and into position for engagement with the lamina. In one embodiment, connecting portion 54 includes a spring-like structure that can be resiliently stretched or elongated to position the hook end portion along the superior lamina surface, and connecting portion 54 resiliently returns toward its pre-stretched state to bias hook end portion 52 into engagement with the superior surface of lamina 16. Engaging member 70 can be configured the same as engaging member 50 for engaging the inferior surface of lower lamina 18. In another embodiment, one of the engaging members 50, 70 includes a spring-like connecting portion that can be elongated while the other does not. In still another form, each of the engaging members 50, 70 are rigid.

Connecting portion 54 can be coupled to spacer member 32 in any suitable manner. In one embodiment, connecting portion 54 is movably coupled to spacer member 32. Connecting portion 54 can be integrally formed with spacer member 32, or can be attached by a fastener, suture, anchor, cable, link, over-molding or other suitable connection. Spacer member 32 can be provided with ears, eyelets, recesses or other suitable structure to facilitate engagement of engaging member 50 to spacer member 32. Connecting portion 74 can be similarly configured.

Figures 3, 4:
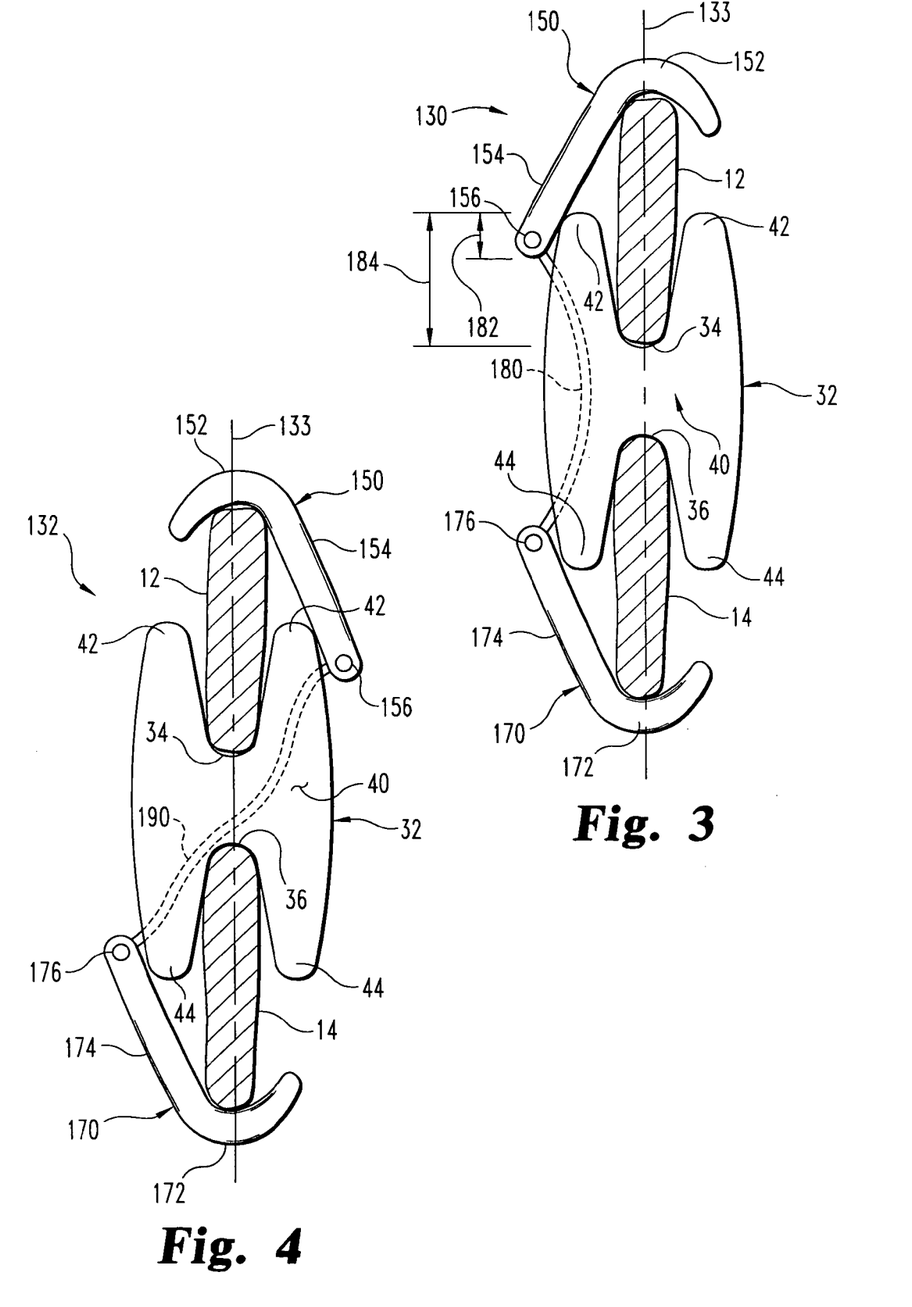
FIG. 3 is an elevation view of another embodiment implant assembly between posterior elements of a spinal motion segment.
FIG. 4 is an elevation view of another embodiment implant assembly between posterior elements of a spinal motion segment.

Referring now to FIG. 3, there is shown a spinal implant assembly 130 having spacer member 32 and engaging members 150, 170 coupled at opposite ends thereof. Spacer member 32 includes a first pair of upper arms 42 defining a concavely curved upper surface 34 extending between arms 42 for nestingly receiving spinous process 12, and a second pair of lower arms 44 defining a concavely curved lower surface 36 between arms 44 for nestingly receiving spinous process 14. Arms 42, 44 extend along the sides of the respective spinous process 12, 14 and prevent spacer member 32 from slipping or moving out of position laterally from between spinous processes 12, 14.

Implant assembly 130 includes an upper engaging member 150 and a lower engaging member 170 for engaging upper lamina 16 and lower lamina 18 in a manner similar to or the same as discussed above with respect to implant assembly 30. Engaging member 150 includes a hook end portion 152 and a connecting portion 154 extending to a location along one of the upper arms 42. Similarly, engaging member 170 includes a hook end portion 172 and a connecting portion 174 extending to a location along one of the lower arms 44. The end 156 of engaging arm 150 is located along arm 42 so that in its implanted position engaging member 150 is not located along the foramen extending along the spinal motion segment. For example, the upper end of arm 42 can be spaced a distance 184 from an anatomical opening to the foramen, while the end 156 of engaging member 150 is spaced a distance 182 from the upper end of arm 42, spacing it above or cephaladly from the opening between vertebrae to the spinal foramen. End 176 of arm 170 can be similarly situated relative to one of the lower arms 44. Other embodiments contemplate arrangements where one or more of the engaging members and connecting member extend along and are exposed to the foramen.

A connecting member 180 extends through spacer member 32, and can be isolated from the foramen by the body of spacer member 32 surrounding connecting member 180. The ends of connecting member 180 are coupled to respective ones of the ends 156, 176 of engaging members 150, 170 to secure engaging members 150, 170 to spacer member 32 while allowing pivoting movement of engaging members 150, 170 relative to spacer member 32.

Referring now to FIG. 4, there is shown another embodiment implant assembly 132. Implant assembly 132 is similar to implant assembly 130 discussed above, and like elements are designated with like reference numerals. However, engaging member 150 is located relative to spacer member 32 on an opposite side of a central axis 133 relative to engaging member 170, whereas in FIG. 3 the engaging member 150 is located on the same side of axis 133 as engaging member 170. In FIG. 4, a connecting member 190 extends trans-axially through spacer member 32 and is coupled to ends 156, 176 of engaging members 150, 170.

In the embodiments in FIGS. 3 and 4, connecting portions 154, 174 can be rigid, although flexible connecting portions 154, 174 are contemplated. Ends 156, 176 can be coupled to connecting member 180, 190 with a pin, fastener, friction fit, adhesive, fusion, crimp, or other suitable connecting arrangement. Ends 156, 176 are located along the respective arms 42, 44 so that their positioning and movement avoids the foramen.

Figure 5:
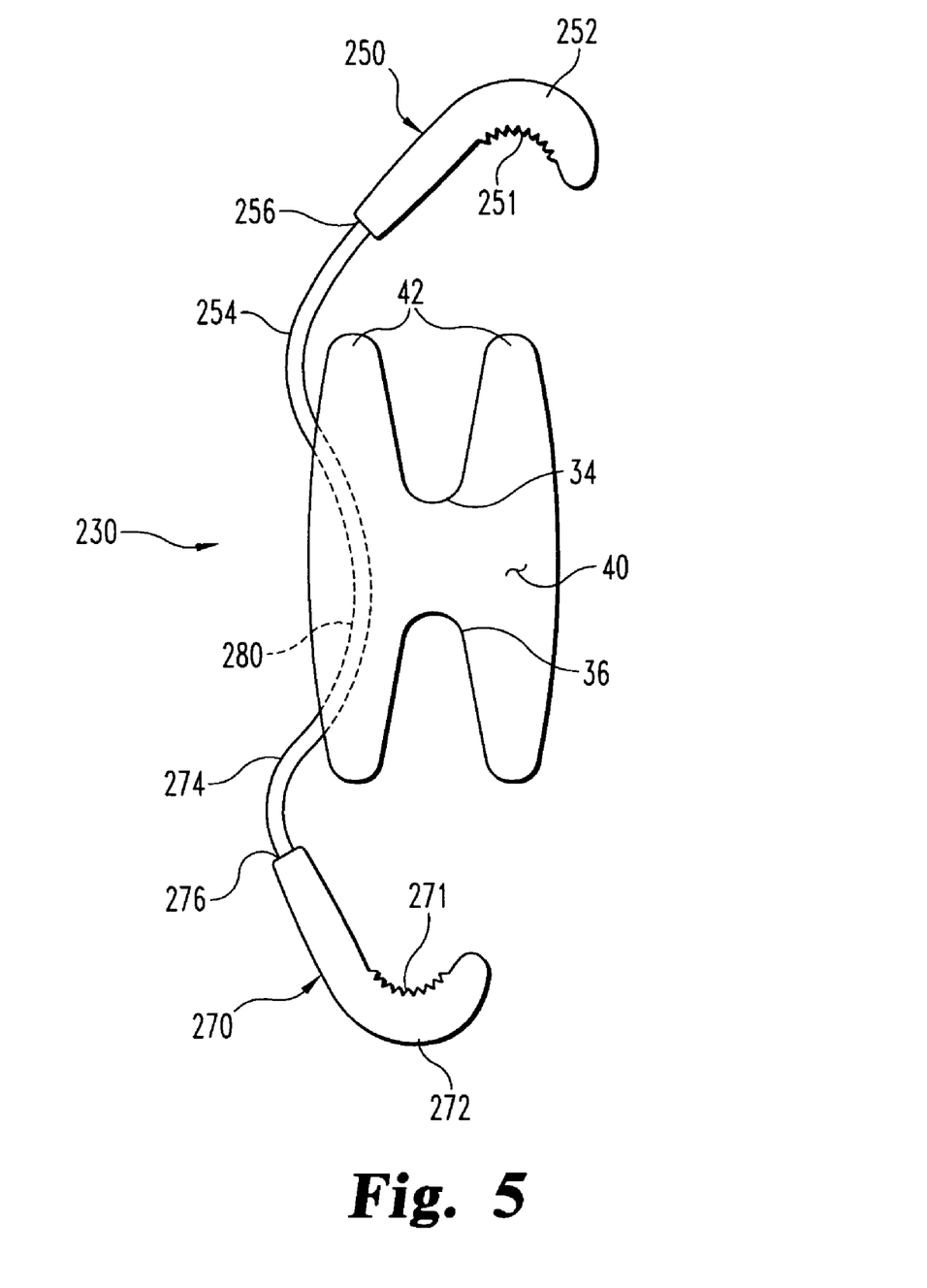
FIG. 5 is an elevation view of another embodiment implant assembly.

In FIG. 5, there is shown another implant assembly 230 including a spacing member 32 with a connecting member 280 extending therethrough. Connecting member 280 includes an upper end 254 extending from the side of one of the arms 42 to a hook end portion 252 of engaging member 250. Connecting member 280 is coupled to hook end portion 252 at connection 256. Connection 256 can include a pin, fastener, friction fit, adhesive, fusion, crimp, or other suitable coupling arrangement. Connecting member 280 further includes a lower end 274 extending from the side of one of the arms 44 to a hook end portion 272 of engaging member 270. Connecting member 280 is coupled to hook end portion 272 at connection 276. Connection 276 can include a pin, fastener, friction fit, adhesive, fusion, crimp, or other suitable coupling arrangement. Engaging members 250, 270 can be located on the same side of a central axis of the body, or can be on opposite sides of the central axis.

Connecting member 280 extends from the body of spacer member 32 so that its connection with respective upper and lower engaging members 250, 270 is spaced from spacer member 32. Connecting member 280 flexibly extends between the respective engaging members 250, 270 to allow movement of engaging member 250, 270. Connecting member 280 can also be stretchable but resilient to provide a spring-like coupling arrangement to assist in maintaining the hook end portions of engaging members 250, 270 in contact with the respective lamina surfaces. Furthermore, hook end portions 250, 270 each include a contact surface 251, 271 with surface features to enhance engagement with the lamina. Such surface features can include spikes, teeth, roughenings, knurlings, surface treatments, etchings, fasteners, or other interruption to enhance engagement and resist movement of the engaging member relative to the lamina surface. Surface features may also be provided with the other embodiment engaging members.

In the implant assembly embodiments utilizing a connecting member, the connecting member extends through the body of spacer member 32 so that it is not exposed to the anatomy outside and adjacent spacer member 32 when implanted. This arrangement avoids exposure of the connecting member to the spinal foramen and neural elements, for example. The connection of the connecting member to the engaging members at locations along the respective arms 42, 44, also avoids exposure to the foramen. The connecting member can be positioned through one or more passages formed in the spacer member, or the spacer member can be over-molded about the connecting member. Various forms for the connecting members are contemplated, including cables, wires, sutures, cords, bands, belts, rigid links or rods, and flexible links or rods, for example.

With respect to the various embodiments described herein, the engaging members can be joined or fixed to the spacer member using various devices and/or techniques, or can be integrally formed with or form an extension of the spacer member. The spacer member can be joined or attached to the engaging member by, for example, sewing the engaging member to the spacer member, thermal welding or bonding, adhesive bonding, three dimensional weaving or braiding, screws, staples, pins, tacks or rivet fixation. Furthermore, the engaging member can be secured to the spacer member either before or after the spacing member is placed between the spinous processes.

The spacer member can be fabricated from components that are flexible or exhibit at least some flexibility. Examples of such components include woven fabric tubing, woven and non-woven mesh, or braided or woven structures, sutures, tethers, cords, planar members, bands, wires, cables, or any other component capable of extending between and supporting the adjacent spinous processes. Additionally, the spacer member may be resilient and/or elastic so it can assume various shapes during and after insertion and attachment.

The spacer member can be made from any biocompatible material, material of synthetic or natural origin, and material of a resorbable or non-resorbable nature. Suitable examples of spacer member material include autograft, allograft or xenograft; tissue materials including soft tissues, connective tissues, demineralized bone matrix and combinations thereof; resorbable materials including polylactide, polyglycolide, tyrosine-derived polycarbonate, polyanhydride, polyorthoester, polyphosphazene, calcium phosphate, hydroxyapatite, bioactive glass, collagen, albumin, fibrinogen and combinations thereof; and non-resorbable materials including polyethylene, polyester, polyvinyl alcohol, polyacrylonitrile, polyamide, polytetrafluorethylene, poly-paraphenylene terephthalamide, polyetheretherketone, cellulose, and combinations thereof.

The engaging members described herein can be made from any one or combinations of biocompatible material, including synthetic or natural autograft, allograft or xenograft tissues, and can be resorbable or non-resorbable nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are carbon-reinforced polymer composites, shape-memory alloys, titanium, titanium alloys, cobalt chrome alloys, stainless steel, and combinations thereof.

In one embodiment, the hook end portion is rigid and made from a metal material, polymer material, or other material exhibiting rigid properties, and the connecting portion is flexible to facilitate positioning of the engaging member along the spinal lamina. In a further embodiment, the connecting portion is resilient and includes a spring or spring-like material that allows stretching for placement of the hook end portion along the lamina and resiliently returns to maintain the hook end portion in contact with the corresponding lamina surface.

While the invention has been illustrated and described in detail in the drawings and foregoing description, the same is to be considered as illustrative and not restrictive in character. All changes and modifications that come within the spirit of the invention are desired to be protected.

What is claimed is:

1. A method for stabilizing a spinal motion segment, comprising:

positioning a spacer member between adjacent upper and lower spinous processes of the spinal motion segment, the spacer member including an upper end contacting an inferior surface of the upper spinous process and a lower end contacting a superior surface of the lower spinous process;

positioning an upper engaging member extending from the upper end of the spacer member in contact with a superior surface of an upper lamina adjacent the upper spinous process; and positioning a lower engaging member extending from the lower end of the spacer member in contact with an interiorly oriented surface adjacent the lower spinous process; and resiliently stretching the upper engaging member before positioning the upper engaging member in contact with the superior surface of the upper lamina.

2. The method of claim 1, wherein the interiorly oriented surface extends along a lower lamina adjacent the lower spinous process, and positioning the lower engaging member includes contacting the inferior surface at the lower lamina with the lower engaging member.

3. The method of claim 2, wherein positioning the upper engaging member and the lower engaging member each includes positioning hooked end portions in contact with the respective lamina surfaces.

4. The method of claim 1, wherein the upper and lower engaging members are movably coupled with the spacer member along respective ones of the upper and lower spinous processes when the spacer member is positioned between the upper and lower spinous processes.

* * * * *